United States Patent [19]

Sick et al.

[11] 4,108,533
[45] Aug. 22, 1978

[54] APPARATUS FOR COMBINING LIGHT EMANATING FROM A LINEAR SCANNING FIELD

[75] Inventors: Erwin Sick, Icking; Angelika Staimer, both of Munich, Fed. Rep. of Germany

[73] Assignee: Erwin Sick Gesellschaft mit beschränkter Haftung Optik-Elektronik, Waldkirch, Fed. Rep. of Germany

[21] Appl. No.: 738,484

[22] Filed: Nov. 3, 1976

[30] Foreign Application Priority Data

Nov. 21, 1975 [DE] Fed. Rep. of Germany ....... 2552331
Nov. 21, 1975 [DE] Fed. Rep. of Germany ....... 2552332
Nov. 21, 1975 [DE] Fed. Rep. of Germany ....... 2552333

[51] Int. Cl.² .................................................. G02B 27/17
[52] U.S. Cl. ........................................ 350/6.7; 356/199
[58] Field of Search ................ 350/7, 6, 160, 199, 350/285, 294, 271–274, 190, 194; 356/199, 200, 120, 209, 237, 276; 358/84; 250/219

[56] References Cited

U.S. PATENT DOCUMENTS

| 2,644,361 | 7/1953  | Birdsall       | 350/194 |
| 3,062,965 | 11/1962 | Sick           | 350/7   |
| 3,138,650 | 6/1964  | Andrychuk      | 350/194 |
| 3,345,120 | 10/1967 | Palmer         | 350/190 |
| 3,506,355 | 4/1970  | Nagel          | 350/194 |
| 3,779,649 | 12/1973 | Bertoya et al. | 356/200 |
| 3,797,908 | 3/1974  | Ward et al.    | 350/7   |
| 3,836,261 | 9/1974  | Clarke         | 356/200 |
| 3,917,414 | 11/1975 | Geis et al.    | 350/190 |
| 4,004,152 | 1/1977  | Obser et al.   | 356/200 |

FOREIGN PATENT DOCUMENTS

| 617,188   | 5/1961 | Canada ................................ 356/200 |
| 2,234,818 | 1/1973 | Fed. Rep. of Germany ........... 356/200 |
| 250,268   | 7/1926 | United Kingdom ..................... 350/190 |

*Primary Examiner*—John K. Corbin
*Assistant Examiner*—B. W. de los Reyes

[57] ABSTRACT

Apparatus for combining light emanating from a linear scanning field on a relatively small receiver via an optical arrangement producing a scanning light spot with a light ray scanning device onto which a light beam impinges, the arrangement further having optical elements of the transmitting beam of rays located in front of the light ray scanning device, a transmitting concave mirror and a receiving concave mirror extending in the scanning direction, and a cylindrical lens parallel to the scanning field and extending in the vicinity of the latter, the transmitting and receiving beams of rays being separated by pupil separation. There is further provided plane mirrors arranged between the concave mirrors and light ray scanning device for bending the receiving beam of rays perpendicular to the scanning direction and in the direction of the intersection point of the optical axis of the transmitting beam of rays located on the light ray scanning device by such an amount that it still strikes the light ray scanning device, but passes beside the optical elements. The curved surface of the cylindrical lens is ground planar in the area of the entry of the transmitting beam of rays, and the receiving concave mirror is displaced relative to the transmitting concave mirror in the sense of shortening the optical path of the receiving light.

17 Claims, 2 Drawing Figures

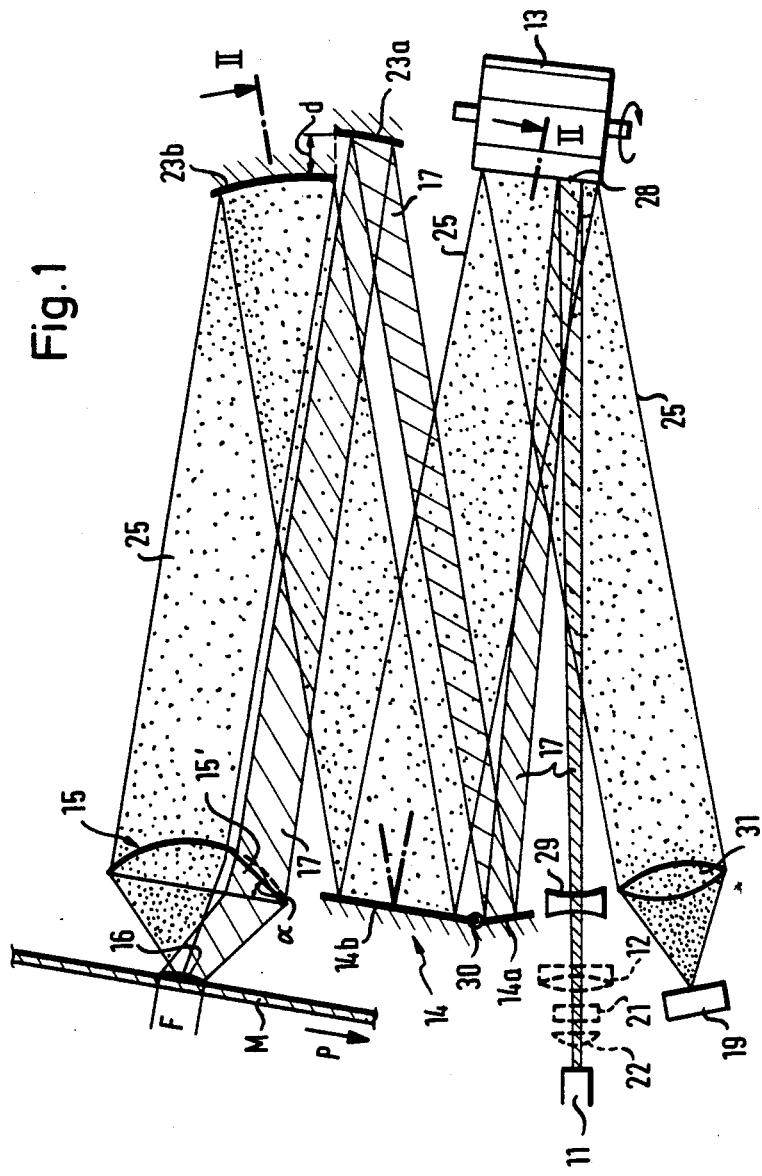

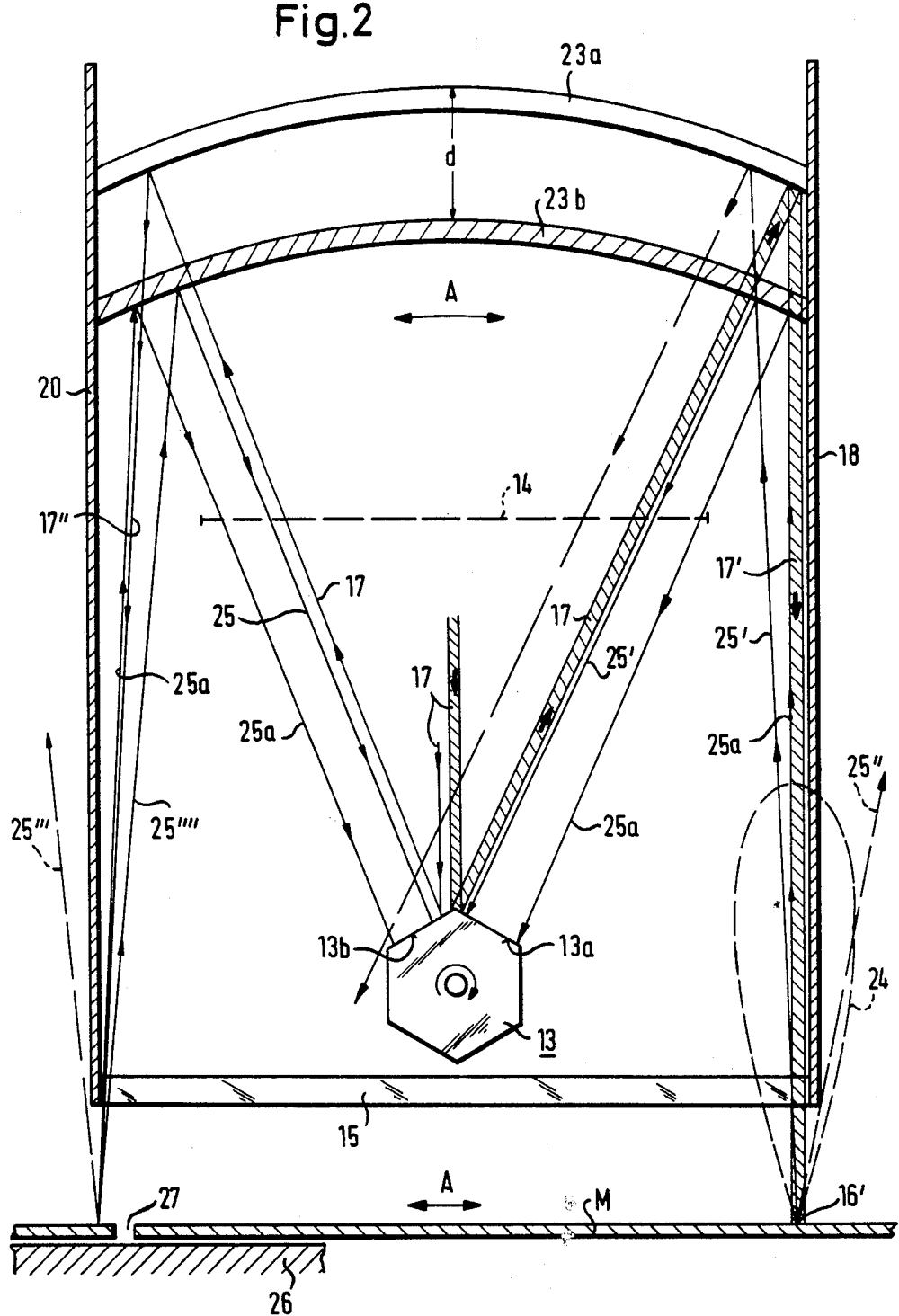

APPARATUS FOR COMBINING LIGHT EMANATING FROM A LINEAR SCANNING FIELD

BACKGROUND OF THE INVENTION

The invention relates to an apparatus for combining light emanating from a linear scanning field on a relatively small receiver via an optical arrangement producing a scanning light spot with a light ray bending device subject to the action of a light beam, a concave mirror extending in the scanning direction and a cylindrical lens parallel to the scanning field and extending in the vicinity of the latter, whereby the transmitting and receiving beams of rays are separated by pupil separation.

In general such apparatus function with a laser as the light source because it emits a narrow parallel beam which is particularly advantageous for producing a fine scanning light spot. In general the laser beam is passed via two crossed cylindrical lenses and an objective to a mirror wheel forming the light ray bending device. The function of the cylindrical lenses is to fan out the laser beam in such a way that it fully illuminates the individual surfaces of the mirror wheel. Advantageously the mirror wheel operates with 12 to 20, and preferably 16 mirror surfaces, which are uniformly distributed over the periphery. In principle it is also possible to use an oscillatory mirror as the light ray bending device.

From the mirror wheel the light beam is deflected via a lamellar plane mirror onto an also lamellar concave mirror, whose focal point or line is located approximately on the reflecting surface of the mirror wheel. The concave mirror directs the transmitting beam of rays which strikes it onto a parallel cylindrical lens located substantially at the spacing of its focal length from a surface on which a linear scanning light spot is to be produced. In general the surface is a web which is to be monitored for faults, such as a metal or paper web surface. The web appropriately moves perpendicular to the rectilinear scanning direction, so that a continuous line scanning of the web is ensured provided that the relationship between web speed and scanning speed is correctly chosen.

Although the receiving beam of rays emanating from the light spot produced on the web can be received and evaluated by a separate receiving device it is preferable for the receiving beam of rays to at least partly be returned in the same way as the transmitting beam of rays to a preferably photoelectrically operating receiving arrangement. The electrical signal emitted by the photoelectric receiver is then a measure of the state of the scanned surface. For example a change in the electrical signal reveals scratches or other faults on a metal surface or faults such as dark spots or holes in the case of a paper web.

If the optical elements of the transmitting beam power are to be used simultaneously for further conducting the receiving beam of rays reference is made to an autocollimating beam path. It is then advantageous for a good separation of the receiving and transmitting beams of rays to use the so-called pupil separation, which means that a part, e.g. a third of at least certain optical elements is used for further conducting the transmitting beam of rays, whilst the remainder, e.g. two-thirds is used for further conducting the receiving beam of rays.

An important problem with autocollimating beam paths is that on the one hand an adequately large light spot with the necessary dimensions is produced on the path for the receiving beams to be reliably reflected back onto the light ray bending device and on the other that there is a reliable spatial separation between the transmitting and receiving beams of rays in the area of the photoelectric receiver. Just as much importance must be attached in this connection to a simple and more particularly compact construction of the apparatus as to the extensive avoidance of susceptibility to vibrations or displacements after relatively long periods. In particular it must be ensured that too much receiving light is not lost in the receiving beam path, so that at the photoelectric receiver there is still a quantity of light which clearly exceeds the background noise for evaluation purposes.

BRIEF SUMMARY OF THE INVENTION

The problem of the present invention is to provide an apparatus of the type indicated hereinbefore, whereby a clean and clear spatial separation between the transmitting and receiving beams of rays is obtained on the side of the light ray bending device located towards the light source, whilst avoiding any increase in the size of the light ray bending device and particularly the mirror wheel, accompanied by a good light yield.

According to the invention this problem is solved in that between the scanning field and the light ray bending device the receiving beam of rays is bent perpendicular to the scanning direction by such an amount relative to the transmitting beam of rays in the direction of the intersection point of the optical axis of the transmitting beam of rays located on the light ray bending device that it still strikes the light ray bending device, but passes by the optical elements of the transmitting beam of rays located in front of the light ray bending device. The light ray bending device is preferably a mirror wheel with 12 to 20 mirror surfaces.

Between the concave mirror and the light ray bending device are advantageously provided lamellar plane mirrors associated with the transmitting or receiving beams of rays and which are tilted somewhat towards one another about an axis running in the scanning direction. A lens and a photoelectric receiver on which the receiving light is concentrated by the lens are advantageously arranged in the receiving beam of rays behind the separation point.

As a result of the measures according to the invention simultaneously two important effects are obtained. Firstly the receiving bundle of rays displaced in the direction of the mirror wheel rotation axis relative to the transmitting beam of rays is superimposed on the transmitting beam of rays due to beam bending in the area of the light ray bending device, so that the areas of the mirror wheel utilised for reflecting and deflecting the transmitting beam of rays are simultaneously used for passing back the receiving light. Secondly due to the striking of the receiving beam of rays at a different angle to the transmitting beam of rays a receiving beam of rays is reflected at a different angle to that at which the transmitting beam of rays strikes the light ray bending device. Thus, at a certain distance from the mirror wheel the transmitting and receiving beams of rays are spaced by a certain distance, so that after the separation point it is merely necessary to provide a photoelectric receiver, preferably combined with a lens in order to measure the receiving light intensity. In conventional manner the photoelectric receiver can be connected to an evaluation electronic system.

The provision of a bending mirror arrangement represents a simple and constructionally advantageous means for obtaining a bending of the receiving beam. The advantageous result of the double utilisation of the mirror wheel surfaces and the separation of the two beams of rays is therefore obtained at a very limited cost.

A bending mirror arrangement for such devices has admittedly already been proposed (German Patent Application No. P25,50,815.0), however, in the arrangement according to the earlier-dated application the bending of the receiving beam path takes place in precisely the opposite direction to that of the present application.

Advantageously the distance between the plane mirrors and the light ray bending device is substantially the same as the distance between the light ray bending device and the objective of the transmitting beam of rays. In this arrangement the same distribution ratio of transmitting and receiving beams of rays exists at the objective as in the bending mirror arrangement.

In order to take account of the relatively large dispersion of the receiving light compared with the sharp focusing of the transmitting light particularly when measuring paper webs the receiving beam of rays is appropriately much wider than the transmitting beam of rays. The receiving beam of rays is preferably twice to four times as wide as the transmitting beam of rays.

Normally the beam of the laser used as the light source is fanned out in such a way by a crossed cylindrical lens arrangement and an objective that it fully illuminates the light ray bending device, particularly the mirror wheel. The cylindrical lens then contracts the light beam to a narrow sharp light spot, which has a slightly elongated shape in the scanning direction. However, there is a reduction in the size of the light spot, for example in the ratio 1:10, particularly perpendicular to the scanning direction, which is in many cases undesirable.

Therefore a further object of the invention is to provide an apparatus of the type indicated hereinbefore in which the said reduction in the size of the light spot perpendicular to the scanning direction does not occur and so that as a result a light spot is obtained which is elongated and not too small perpendicular to the scanning direction, i.e. in the direction of movement of the material web to be monitored.

According to the invention this problem is solved in that the curved surface of the cylindrical lens is ground flat in the entry area of the transmitting beam of rays. The flat surface portion preferably has a slope which is the same as the average inclination of the original curvature of the cylindrical lens in this area.

Thus, according to the invention, in the transmitting part the action of the cylindrical lens as a size-reducing optical element is lost. However, the deflecting action of the cylindrical lens is intentionally maintained, so that at the desired point in the scanning field a much larger elongated light spot is obtained in the direction of movement of the web, but which is located in the area of the focal line of the cylindrical lens. Therefore a parallel beam of rays emanates from the receiving part of the cylindrical lens, running parallel to the transmitting beam of rays.

According to an advantageous embodiment the wedge-shaped part of the cylindrical lens takes up one-fifth to one-third and preferably one-quarter of the total width of the cylindrical lens. This has the advantage that a much larger area of the cylindrical lens is available for the receiving beam of rays. This takes account of the fact that the transmitting beam of rays is sharply focused, whereas the light reflected from the material web generally has a pronounced dispersion.

Whereas on not inserting any lenses in the transmitting beam of rays due to the action of the concave mirror in the scanning field a punctiform light spot is produced according to a further embodiment a line of light extending in the direction of movement of the material web can be obtained in that between the light source formed by a laser and the light ray bending device a dispersing element is provided which fans out the transmitting beam of rays by such an amount that the scanning light spot assumes an elongated shape extending perpendicular to the scanning direction.

A further problem with line scanners is that the receiving signal is often extemely weak in the area of the peripheral rays, so that the latter can frequently not be used for fault monitoring. This is particularly disadvantageous if a plurality of line scanning devices are directly juxtaposed for monitoring relatively wide material webs. In this case it is impossible to take account of dead zones between the individual line scanning devices. The hitherto adopted remedy has been to stagger the individual juxtaposed line scanners and to arrange them with a certain overlapping, but this is both very space consuming and means that different lines of the web are scanned at one time. This makes the subsequent evaluation offaults more difficult.

Therefore a further object of the invention is to provide an apparatus of the type indicated hereinbefore in which the peripheral rays which also occur directly at the end of the scanning area also lead to a receiving signal at the photoelectric receiver permitting a completely satisfactory fault evaluation.

According to the invention this problem is solved in that the concave mirror is sub-divided into a transmitting and receiving concave mirror and the receiving concave mirror is displaced relative to the transmitting concave mirror with the object of shortening the optical path of the receiving light. A prerequisite for the functioning of this apparatus is that the material web surface does not reflect in a precisely specular manner, but also has a certain light dispersion area about the precisely speculating reflection. However, this condition is fulfilled with virtually all surfaces and even in the case of smooth metal surfaces, unless the latter are especially worked and particularly ground to obtain an absolutely specular reflection. As a result of the construction according to the invention a much larger part of the light dispersed within the apparatus is detected than without the indicated displacement of the associated mirror wheel surface, so that an electrical signal adequate for fault evaluation is still available at the photoelectric receiver even in the area of the peripheral scanning beams. The scanning transmitting beams can therefore by fully utilised up to the edge of the housing.

The displacement appropriately takes place in the direction of the cylindrical lens, whereby ideally displacement takes place along the bisector of the angle of the emergent and incident beam.

Displacement must take place by such an amount that from the light spots produced by the peripheral rays of the transmitting beam of rays a considerable part of the reflected light strikes the same surface of the light ray bending device by which the transmitting beam of rays is reflected.

If a plurality of apparatuses according to the invention are juxtaposed a small gap exists between the scanning areas because the optical elements, particularly the concave mirrors and the cylindrical lenses can only extend up to the housing wall. Thus, in the most favourable case there is a gap of approximately double the housing wall thickness between the individual scanning areas. In order to bridge this small gap a particularly preferred embodiment of the invention provides for the light ray bending device being located somewhat within the focal length of the transmitting concave mirror in such a way that due to the divergent peripheral rays the scanning range is extended somewhat. It is thus achieved that the scanning areas of adjacent apparatuses are contiguous or even overlap slightly.

The transmitting concave mirror is preferably significantly narrower than the receiving concave mirror, whereby the transmitting concave mirror width is appropriately a quarter to a half, preferably a third of the receiving concave mirror width. The displacement of the two concave mirrors must be approximately 2 to 10% and preferably 5% of the concave mirror focal length.

The concave mirrors are completely identical, except for the width, i.e. particularly with regard to the focal length. The arrangement is in particular as if the two concave mirrors were obtained by cutting open a single concave mirror in the scanning direction and displacing the two parts in the direction of the bisector of the angle of the emergent and incident beam.

BRIEF DESCRIPTION OF THE DRAWINGS

The invention is explained in exemplified manner hereinafter with reference to the drawings, wherein show:

FIG. 1 a schematic side view of a preferred embodiment of the apparatus according to the invention and FIG. 2 a partly cut away view along the line II—II of FIG. 1, whereby the two beam paths bent at mirror arrangement 14 have been shown in extended form for reasons of simplicity and mirror arrangement 14 is only indicated by a dotted line.

DETAILED DESCRIPTION OF THE PREFERRED EMBODIMENTS

According to the drawings the narrow light beam having only a slight divergence emitted by laser 11 passes via a divergent cylindrical lens 29 to a mirror wheel 13. The divergent lens 29, which could also be replaced by a convergent cylindrical lens, gives the laser beam a relatively small divergence, as can be seen in FIG. 1.

The transmitting beam of rays 17 strikes eg. on one half of a mirror wheel 13, which is slightly tilted in the indicated manner, whereby the intersection point of optical axis of the transmitting beam of rays 17 is indicated at 28.

The slightly tilted mirror wheel 13 reflects the transmitting beam of rays to a plane mirror 14a which is constructed in lamellar form whose longitudinal axis extends perpendicular to the drawing plane. According to FIG. 2 the length of mirror 14a must be sufficiently large that it can detect all the beams of light reflected by mirror wheel 13 within the scanning range.

From the once again somewhat tilted plane mirror 14a the transmitting beam of rays 17 is reflected to a first lamellar concave mirror 23a which is also perpendicular to the drawing plane and whose focal point or line is located substantially on the reflecting surface of mirror wheel 13. Preferably, however, the reflecting surface of mirror wheel 13 is slightly inside the focal length of concave mirror 23a in such a way that the beam reflected by concave mirror 23a has a slight divergence, as is intimated in the left-hand half of FIG. 2.

A cylindrical lens 15, whose axis is parallel to the scanning direction indicated by A and which substantially has a distance from the surface of material web M corresponding to its focal length is located directly in front of web M which is to be monitored by the apparatus according to the invention for faults and which moves continually in the direction of arrow P.

According to the invention the receiving beam of rays 17 only strikes a portion 15' of cylindrical lens 15, within which is ground the curvature of lens 15 indicated by dotted lines in FIG. 1, in such a way that a planar surface is formed in this area and is represented by continuous lines. Thus, the transmitting beam of rays 17 strikes on an optical web 15', whose wedge angle is designated by $\alpha$. The wedge angle corresponds to the average inclination of the ground-away curved portion of cylindrical lens 15.

As a result of the measure according to the invention the transmitting beam of rays 17 is only bent towards the scanning field F in the indicated manner, without there being any contraction of the beam of rays 17, as would be the case if cylindrical lens 15 were not ground-away in the area of wedge 15. Thus, in the desired manner a not too small light spot 16 is obtained in scanning field F. If the cylindrical lens was not ground-away in area 15' the light spot would be reduced in size by up to a factor of 10, this being prevented by the present invention.

As a result of the inventive selection of wedge angle light spot 16 appears in the area of the focal line of cylindrical lens 15. So that the light scattered back into cylindrical lens 15 by light spot 16 is combined into a substantially parallel receiving beam of rays, as can be seen in FIG. 1. The receiving beam of rays strikes a further concave mirror 23b, which is staggered relative to the transmitting concave mirror 23a by a portion $d$ in the direction of cylindrical lens 15. The receiving concave mirror 23b is also wider than the transmitting concave mirror 23a in order to be able to detect as much light as possible. In addition, the two concave mirrors 23a 23b are identical, as regards their extension perpendicular to the drawing plane in FIG. 1 and their focal length. With reference to the displacement $d$ it must be ensured that beams of light striking the two mirrors 23a 23b in parallel manner continue to be reflected parallel to one another.

Following the reflection of the receiving beam of rays 25 on concave mirror 23 this strikes a further plane mirror 14b, which in the represented manner is made much wider than plane mirror 14a and is tilted relative to plane mirror 14a by a certain amount about an axis 30 which is perpendicular to the drawing plane of FIG. 1. Thus a bending mirror arrangement 14 is provided which comprises the two plane mirrors 14a, 14b. The bending angle is thereby so large that the receiving light beam 25 reflected on plane mirror 14b is directed as completely as possible onto the reflecting surface of mirror wheel 13. The receiving beam of rays 25 thereby undergoes a displacement in the direction of the intersection point 28 of the optical axis of the transmitting beam of rays 17. As a result of the bending angle between plane mirrors 14a and 14b the receiving beam of rays 25 is reflected in the manner indicated in FIG. 1 at mirror wheel 13 at an angle which differs from the incident angle of the transmitting beam of rays 17, so that after a certain distance there is complete separation between the transmitting beam of rays 17 and the receiving beam of rays 25. After the separation point a convergent lens 31 is arranged in the receiving beam of rays 25, in whose focal point is located a photoelectric receiver 19, constructed for example as a photomultiplier, at whose output an electrical signal appears, which is representative for the state of the just scanned point in the scanning field F.

The transmitting beam path 17 shown in FIG. 1 has the advantage that the narrow construction of the laser beam can be directly utilised for producing a light spot 16. The divergence caused by cylindrical lens 29 is thereby selected in such a way that light spot 16 has an elongated shape in the direction of movement P. Light spot 16 is in particular a line extending in the direction of movement P, which is for example advantageous in the determination of longitudinal scratches on the surfaces of metal sheets.

It is also possible to use crossed cylindrical lenses 21, 22 and an objective 12 in place of cylindrical lens 29. These elements are shown by dotted lines in FIG. 1 without taking account of the actual spacings and focal lengths of these optical elements. When using the laser beam fanning cylindrical lenses 21, 22 and objective 12 completely illuminated by said cylindrical lenses the construction of cylindrical lens 15 as a wedge 15' must be lost on one side, in order to obtain a narrow light spot at 16. The separation of the transmitting and receiving beams of rays 17 25 can also be carried out in accordance with the invention in this arrangement, whereby the convergent lens 31 is appropriately level with objective 12 and the individual parameters are selected in such a way that the complete separation of transmitting beam of rays 17 and receiving beam of rays 25 takes place level with objective 12.

Cylindrical lens 29 must be dimensioned in such a way that the transmitting beam 17 has a sufficient divergence for forming the elongated light spot 16, whilst taking account of the convergence properties of concave mirror 23a.

FIG. 2 shows the action of the displacement d of the two concave mirrors 23a 23b. This displacement is important in order to obtain an adequate return signal from the peripheral rays 17'. In the area of one housing wall 18, FIG. 2 shows a peripheral ray 17' located directly on the wall, which is produced in the represented manner by reflecting the transmitting beam of rays 17 at transmitting concave mirror 23a. The peripheral ray 17' passes through cylindrical lens 15 onto the surface of material web M where a light spot 16' is produced.

It is now assumed that the surface of material web M has reflective properties, as are schematically indicated by lobe 24. The reflection intensity is indicated by straight lines drawn from light spot 16' in the individual directions up to lobe 24. The length of the straight lines from the pedal point at 16' up to the edge of the lobe is a measure of the reflecting intensity. It is clear for example that the light beams reflected from spot 16' in direction 25" are lost for evaluation purposes, because they strike the housing wall 18 or even pass outside housing wall 18. However, for example, a further inwards reflected receiving light beam 25' passes back to the transmitting concave mirror 23a. Due to the different inclination relative to the surface of web M compared with peripheral ray 17' this reflected beam would no longer strike that surface 13a of mirror wheel 13 from which the transmitting beam of rays 17 was reflected. In fact the receiving beam of rays 25' reflected at 23a would completely pass by the mirror wheel 13, as indicated by dotted lines.

However, on displacing the receiving concave mirror 23b by a portion d in the direction of the bisector of the angle between the emergent and incident rays the receiving light beam 25' reflected by surface M would pass to surface 13a of mirror wheel 13 in the manner indicated by continuous lines. Thus, light is available which in the manner shown in FIG. 1 reaches photoelectric receiver 19.

The displacement d of transmitting and receiving concave mirrors 23a 23b is also important if a plurality of apparatuses according to the invention are contiguously juxtaposed and a scanning gap is to be avoided between two juxtaposed apparatuses. To this end in accordance with the left-hand half of FIG. 2 mirror wheel 13 is arranged somewhat inside the focal length of the transmitting concave mirror 23a in such a way that particularly in the peripheral areas the peripheral rays 17" have a certain divergence which is at least sufficiently large for the scanning range to be slightly wider than the housing. In the case of a completely specular surface of material web M the light would for example be reflected along the dotted line 25''' outside housing wall 20. In the case of a surface M with a dispersion lobe as shown at the right at 24 light would also be reflected back into the inside of housing 18, 20, for example in the direction of line 25'''', where it strikes the receiving concave mirror 23b from where it is deflected to surface 13b of mirror wheel 13, which is also being struck by the transmitting beam of rays 17. It is therefore clear that even when using a divergent scanning beam path sufficient light still gets back to the mirror wheel surface 13b subject to the action of the transmitting light beam 17, when using the construction according to the invention. However, it is necessary that the surface of material web M is not absolutely specular, but instead has a certain scattering range, as is indicated for example by dispersion lobe 24. However such dispersions are generally available in the case of paper webs and conventional metal surfaces in rolling mills.

The line scanning apparatus according to the invention is particularly suitable for detecting holes in paper webs. In this case it is a question of the paper web M being guided over a, for example, metal roller 26, whose surface reflects well, but not in an absolutely specular manner. The dispersion characteristics of such a surface are preferably like dispersion lobe 24. FIG. 2 schematically shows a small cut away portion of such a roller 26. If there is a hole 27 in the paper web the light passing through this hole onto the surface of roller 26 is at least mainly deflected back to photoelectric receiver 19, if, as is indicated in FIG. 2, hole 27 is located at the edge of the apparatus in the area of one of the walls 18, 20. Thus, a hole 27 in paper web M leads to a light signal at photoelectric cell 19. A dark point on paper web M would lead to a dark signal. The arrangement according to the invention therefore makes it possible to differentiate in simple manner holes and dark points on paper webs. It is even possible for monitoring very wide paper webs to juxtapose a plurality of the apparatuses according to the invention, by making a wall 18 of a first apparatus directly contiguous with a wall 20 of an identically constructed second apparatus and so on.

The amount of displacement $d$ is appropriately substantially so large that the peripheral rays 17' 17", reflected back into themselves as receiving rays 25a strike a terminal area (viewed in the circumferential direction) of the associated mirror wheel surface 13a, 13b, when the transmitting beam 17 strikes the other terminal area of the same surface 13a or 13b, as is shown in FIG. 2. This leads to an optimum illumination of the mirror wheel and therefore to an optimum light yield.

The invention is not limited to the embodiments described and represented hereinbefore and various modifications can be made thereto without passing beyond the scope of the invention.

What is claimed is:

1. In an apparatus for combining light emanating from a linear scanning field on a relatively small receiver via an optical arrangement producing a scanning light spot with a light ray scanning device onto which a light beam impinges, said arrangement further having optical element means of the transmitting beam of rays located in front of the light ray scanning device, a concave mirror means extending in the scanning direction, and a cylindrical lens parallel to the scanning field and extending in the vicinity of the latter, and in which arrangement the transmitting and receiving beams of rays are separated by pupil separation, characterized by plane mirrors associated with the transmitting and receiving beams of light between the scanning field and the light ray scanning device for bending the receiving beam of rays perpendicular to the scanning direction and in the direction of the intersection point of the optical axis of the transmitting beam of rays located on the light ray scanning device by such an amount that it still strikes the light ray scanning device, but passes beside said optical element means, said concave mirror means comprising a transmitting concave mirror and a receiving concave mirror, and said plane mirrors being arranged between said concave mirrors and said light ray scanning device and tilted towards one another about an axis directed in the scanning direction.

2. Apparatus according to claim 1, wherein said light ray scanning device is a mirror wheel.

3. Apparatus according to claim 1, wherein a lens and a photo receiver are arranged in the receiving beam of rays behind the separating point.

4. Apparatus according to claim 1, wherein the distance between said means for bending the receiving beam of rays and the light ray scanning device is approximately the same as the spacing between the light ray scanning device and the optical element means of the transmitting beam of rays.

5. Apparatus according to claim 1, wherein the receiving beam of rays is significantly wider than the transmitting beam of rays.

6. Apparatus according to claim 5, wherein the receiving beam of rays is approximately three times as wide as the transmitting beam of rays.

7. Apparatus according to claim 5, wherein an optionally somewhat fanned-out laser beam is used as the transmitting beam of rays.

8. In an apparatus for combining light emanating from a linear scanning field on a relatively small receiver via an optical arrangement producing a scanning light spot with a light ray scanning device onto which a light beam impinges, said arrangement further having a concave mirror extending in the scanning direction, and a cylindrical lens parallel to the scanning field and extending in the vicinity of the latter, and in which arrangement the transmitting and receiving beams of rays are separated by pupil separation, characterized in that said concave mirror means comprises a transmitting and a receiving concave mirror, the receiving concave mirror being displaced relative to the transmitting concave mirror in the sense of shortening the optical path of the receiving light.

9. Apparatus according to claim 1, wherein the displacement takes place in the direction of the cylindrical lens.

10. Apparatus according to claim 8, wherein the displacement takes place by a distance such that from the light spot produced by the peripheral rays of the transmitting beam of rays a considerable portion of the reflected light strikes the same surface of the light ray scanning device by which the transmitting beam of rays is reflected.

11. Apparatus according to claim 8, wherein the light ray scanning device is arranged somewhat within the focal length of the transmitting concave mirror in such a way that as a result of the divergent peripheral rays the scanning range is somewhat extended.

12. Apparatus according to claim 8, wherein the transmitting concave mirror is made substantially narrower than the receiving concave mirror.

13. Apparatus according to claim 12, wherein the transmitting concave mirror has one-quarter to one-half and preferably one-third of the width of the receiving concave mirror.

14. Apparatus according to claim 8, wherein the displacement of the two concave mirrors is approximately 2 to 10% and preferably 5% of the concave mirror focal length.

15. In an apparatus for combining light emanating from a linear scanning field on a relatively small receiver via an optical arrangement producing a scanning light spot with a light ray scanning device onto which a light beam impinges, said arrangement further having a concave mirror extending in the scanning direction, and a cylindrical lens parallel to the scanning field and extending in the vicinity of the latter, and in which arrangement the transmitting and receiving beams of rays are separated by pupil separation, characterized in that the curved surface of the cylindrical lens is ground planar in the area of the entry of the transmitting beam of rays, the planar portion of the surface of the cylindrical lens having an inclination wedge which is the same as the average slope of the original curvature of the cylindrical lens in this area.

16. Apparatus according to claim 15, wherein the wedge shaped part of the cylindrical lens takes up approximately one-fifth to one-third and preferably one-quarter of the total width of the cylindrical lens.

17. Apparatus according to claim 15, wherein there is provided a light source formed by a laser, and between said light source and light ray scanning device there is provided a dispersion element which fans out the transmitting beam of rays by such an amount that the scanning light spot assumes an elongated shape perpendicular to the scanning direction.

* * * * *